United States Patent
Ochoa Gomez et al.

(10) Patent No.: US 9,975,827 B2
(45) Date of Patent: May 22, 2018

(54) METHOD FOR MANUFACTURING 2,3-BUTANEDIOL

(71) Applicant: FUNDACION TECNALIA RESEARCH & INNOVATION, San Sebastian-Guipuzcoa (ES)

(72) Inventors: Jose Ramon Ochoa Gomez, San Sebastian-Guipuzcoa (ES); Silvia Gil Rio, San Sebastian-Guipuzcoa (ES); Francisca Rio Perez, San Sebastian-Guipuzcoa (ES); Leire Lorenzo Ibarreta, San Sebastian-Guipuzcoa (ES); Cristina Dineiro Garcia, San Sebastian-Guipuzcoa (ES); Tomas Roncal Martinez, San Sebastian-Guipuzcoa (ES)

(73) Assignee: FUNDACION TECNALIA RESEARCH & INNOVATION, San Sebastian-Guipuzcoa (ES)

( * ) Notice: Subject to any disclaimer, the term of this patent is extended or adjusted under 35 U.S.C. 154(b) by 0 days. days.

(21) Appl. No.: 15/327,941

(22) PCT Filed: Jul. 23, 2014

(86) PCT No.: PCT/ES2014/070598
§ 371 (c)(1),
(2) Date: Jan. 20, 2017

(87) PCT Pub. No.: WO2016/012634
PCT Pub. Date: Jan. 28, 2016

(65) Prior Publication Data
US 2017/0327443 A1 Nov. 16, 2017

(51) Int. Cl.
| C07C 29/145 | (2006.01) |
| C07C 31/20  | (2006.01) |
| B01J 23/46  | (2006.01) |
| B01J 23/44  | (2006.01) |
| B01J 23/42  | (2006.01) |
| B01J 23/755 | (2006.01) |

(52) U.S. Cl.
CPC ............ *C07C 29/145* (2013.01); *B01J 23/42* (2013.01); *B01J 23/44* (2013.01); *B01J 23/462* (2013.01); *B01J 23/755* (2013.01)

(58) Field of Classification Search
CPC .................................................. C07C 29/145
See application file for complete search history.

(56) References Cited

U.S. PATENT DOCUMENTS 5,684,215 A 11/1997 Horn et al.

FOREIGN PATENT DOCUMENTS

EP 0 405 956 6/1990

OTHER PUBLICATIONS

Zuo, X. et al. "Modification effect of metal cations on the stereoselective hydrogenation of 2,3-butanedione" Catalysis Letters vol. 71, No. 3-4, 2001 (Year: 2001).*
Ishiyama, J. et al. "Catalytic hydrogenation of 2,3-butanedione over group VIII metal catalysts" Nippon Kagaku Kaishi, Issue: 6, pp. 771-773, Journal, 1991 (Year: 1991).*
Ishiyama, J. et al. "Catalytic hydrogenation of 2,3-butanedione over group VIII metal catalysts" Nippon Kagaku Kaishi, Issue: 6, pp. 771-773, Journal, 1991; English Abstract (Year: 1991).*
Burk, M. J. et al. "Efficient rhodium-catalyzed hydrogenation of aldehydes and ketones" Tetrahedron Letters vol. 35, Issue 28, Jul. 11, 1994, pp. 4963-4966 (Year: 1994).*
Hattori, K. et al. Tetrahedron 57, 2001, 4817-4824 (Year: 2001).*
Margitfalvi, et al.; "*Influence of Achiral Tertiary Amines on the Enantioselective Hydrogenation of α, β-diketones Over Cinchonidine-Pt/Al₂O₃ Catalyst*"; Chemical Industries, vol. 104, 2005, pp. 535-540 (6 pages).
Slipszenko, et al.; "*Enantioselective Hydrogenation—V. Hydrogenation of Butane-2,3-dione and of 3-Hydroxybutan-2-one Catalysed by Cinchona-Modified Platinum*"; Journal of Catalysis, vol. 179, No. 1, 1998, pp. 267-276 (10 pages).
Reppe, et al.; "*Äthinylierung IV*"; Justus Liebigs Annalen Der Chemie, vol. 596, No. 1, 1955, pp. 38-79 (42 pages).
Grivsky Eugène; "*Oxydation des deux formes diastéréoisomères du butanediol-2.3 par la Bactérie du Sorbose et le Mycoderma aceti*"; Bulletin De La Société Chimique de Belgique, vol. 51, 1942, pp. 63-112 (54 pages).
European Patent Office Searching Authority, PCT/ES2014/070598 International Search Report and Written Opinion, dated Mar. 2015, 12 pages.

* cited by examiner

*Primary Examiner* — Medhanit W Bahta

(57) ABSTRACT

The invention relates to a process for manufacturing 2,3-butanediol by hydrogenation of acetoin using a heterogeneous hydrogenation catalyst and under conditions leading to a selectivity higher than 90%. In a preferred embodiment, the hydrogenation is carried out in the presence of no solvent or in the presence of a solvent like water or 2,3-butanediol.

17 Claims, No Drawings

METHOD FOR MANUFACTURING 2,3-BUTANEDIOL

FIELD OF THE INVENTION

The present invention is related to a process for manufacturing 2,3-butanediol by hydrogenation of acetoin using hydrogen and heterogeneous hydrogenation catalysts, both in the absence and in the presence of a solvent selected from water, a water-soluble non-acidic solvent, and mixtures thereof, especially heterogeneous supported metal noble catalysts.

BACKGROUND OF THE INVENTION 2,3-Butanediol (2,3-BDO) is a chemical which has important present and potential industrial applications, e.g. as antifreeze, as raw material for methyl ethyl ketone and 1,3-butadiene manufacturing by dehydration, and even as liquid fuel due to its heating value of 27198 kJ·kg$^{-1}$ (Flickinger, M. C., *Biotechnol. Bioeng.* 1980, 22, 27) which is comparable to those of methanol (22081 kJ·kg$^{-1}$) and ethanol (29055 kJ·kg$^{-1}$). Other potential applications include the manufacture of printing inks, perfumes, fumigants, moistening and softening agents, explosives and plasticizers, and as a carrier for pharmaceuticals (Xiu, Z. L., Zeng, A. P., Present state and perspective of downstream processing of biologically produced 1,3-propanediol and 2,3-butanediol. *Appl. Microbiol. Biotechnol.* 2008, 78, 917-926).

Almost the totality of the 2,3-BDO manufacturing processes described are based on fermentation of carbohydrates using many bacterial species as shown by both academic (Xiao-Jun J., He H., Ping-Kai O., Microbial 2,3-butanediol production: A state-of-the-art review. *Biotechnology Advances* 2011, 29, 351-364) and patent (e.g., WO 2014013330 A2, WO 2013076144 A2, U.S. Pat. No. 8,455, 224 B2, US 20130316418 A1, WO 2009151342 A1, EP 1897955 B1, WO2009151342A1, U.S. Pat. No. 7,968,319 B2, U.S. Pat. No. 2,389,263 A, KR20130091080 (A)) literature. All these methods have in common as main drawbacks a very low 2,3-BDO productivity, usually ranging from 1 to 3 g/L/h, and a low 2,3-BDO titer in the final culture broth, usually below 120 g/L, and much more usually below 100 g/L. The latter fact, together with the highly complex chemical composition of the culture broth, lead to cumbersome methods for isolation and purification of 2,3-BDO with the corresponding economic penalties.

There are also some chemical routes for obtaining 2,3-BDO. Thus, in CN 103193596A 2,3-BDO is synthesized from a mixture of an alcohol (e.g., methanol, ethanol, propanol and butanol) and mixed C4 hydrocarbons by oxidation with hydrogen peroxide in the presence of titanium silicalite modified with aluminum oxide as catalyst. However, this process leads to a low 2,3-BDO selectivity of 41%. In JPH0441447 (A) 2,3-BDO is produced by means of photocatalyst by irradiating ethanol with light resulting from a high-intensity ultraviolet laser in the presence of hydrogen peroxide, process which is not industrially feasible.

The process of the present invention overcomes the above mentioned drawbacks by using as raw material acetoin (3-hydroxybutanone), an α-hydroxy ketone, which is reduced with hydrogen to 2,3-BDO using a heterogeneous hydrogenation catalyst optionally in the presence of a solvent.

In *Org. Lett.*, 2007, 9 (13), 2565-2567, T. Ohkuma et al describe the asymmetric hydrogenation of a series of α-hydroxy aromatic ketones in methanol catalyzed by Cp*Ir(OTf)(MsDPEN) (MsDPEN=N-(methanesulfonyl)-1,2-diphenylenediamine). However, this procedure for α-hydroxy aromatic ketones hydrogenation has some drawbacks like the use of a homogeneous catalyst which makes much more complex the isolation of the product.

In EP 0405956A1 a process for the catalytic hydrogenation of α-hydroxy ketones is described. Dihydroxyacetone and eruthrulose are the only α-hydroxy ketones mentioned, which are reduced to the corresponding alcohols, e.g. glycerol if dihydroxyacetone is the starting α-hydroxy ketone, in a heterogeneous liquid phase reaction medium which contains a carboxylic acid as strong selectivity enhancer to the alcohol. If no carboxylic acid is added selectivity is lower than 75%.

Surprisingly, the present inventors have found that in the process of the present invention a selectivity higher than 90% is achieved with no carboxylic acid added, which is not apparent for a person skilled in the art. This leads to a very important industrial additional advantage because isolation of the target chemical, 2,3-butanediol in the present invention, can be carried out in a much easier and cheap way. On the other hand, the use of carboxylic acids as selectivity enhancers as those used in EP 0405956A1, citric and acetic acids, can affect negatively to the stability of the metal catalyst employed, in particular to catalysts comprising a Group VIII metal as those used in EP 0405956A1. This is because the carboxylic acids, like, e.g., citric acid act as chelating agents and, consequently, losses of metal catalyst from the support by lixiviation can easily occur. This important drawback is also avoided in the process of the present invention as shown in examples 37 and 38 in which a catalyst was repeatedly recycled with no loss in metal content.

DETAILED DESCRIPTION OF THE INVENTION

In one aspect, the present invention is related to a process for manufacturing 2,3-butanediol by hydrogenation of acetoin using hydrogen and a heterogeneous hydrogenation catalyst in the absence of any carboxylic acid. The process can be carried out in the absence of any solvent or in the presence of a solvent selected from water, a water-soluble non-acidic solvent, and mixtures thereof.

The process can be carried out by mixing acetoin, hydrogen, a heterogeneous hydrogenation catalyst and, optionally, a solvent, under the suitable reaction conditions of temperature, pressure and reaction time (or residence time for continuous operation).

The reaction is carried out batchwise, semicontinuously or continuously at hydrogen partial pressures from 1 MPa to 10 MPa, temperatures from room temperature to 200° C.

As herein used, the term "a water soluble non-acidic solvent" means a water soluble organic solvent without any acid group like carboxylic, sulfonic, sulfinic, phosphoric, phosphonic, phenolic and boronic acid groups. According to a particular embodiment the water soluble non-acidic solvent is selected from the group of aliphatic and cycloaliphatic mono- and polyhydric alcohols.

Acetoin has an asymmetric carbon and consequently it is a chiral molecule. Any one of the stereoisomers as well as their mixtures can be used as a raw material in the process of the present invention. Accordingly, throughout the present invention the term acetoin encompasses its enantiomers as well as mixtures thereof in any proportions, like a racemic mixture.

According to the present invention, acetoin hydrogenation is carried out with heterogeneous hydrogenation catalysts, preferably a heterogeneous supported metal noble catalyst. Catalysts comprising nickel, such as Raney nickel and sponge nickel, can be also used as heterogeneous catalysts.

The noble metals can be selected from the group consisting of Ru, Rh, Pd, and Pt, and their mixtures.

According to a preferred embodiment the noble metal is ruthenium.

According to another preferred embodiment the noble metal is platinum.

Examples of inert supports include, but are not limited to, carbon, graphite, graphene, graphene oxide, alumina and silica. According to a preferred embodiment the support is carbon. According to another preferred embodiment the support is alumina.

A preferred catalyst is ruthenium supported on carbon. A further preferred catalyst is platinum supported on carbon. Another preferred catalyst is ruthenium supported on alumina. A still further preferred catalyst is platinum supported on alumina.

Other particular catalysts are palladium supported on carbon or palladium supported on alumina. A further particular catalyst is ruthenium supported on graphene.

The catalyst concentration may vary within a broad range, however is typically adjusted in the range from 0.005 wt % to 0.5 wt % (based on the amount of active metal relative to that of acetoin), more preferably from 0.01 wt % to 0.5 wt %, and most preferably from 0.01 wt % to 0.25 wt %. In relation with the catalyst concentration it has to be pointed out that from the examples given in EP 0405956A1 it can be deduced that catalysts are used in a high concentration between 0.62 wt % (Ru 5%/C) and 8 wt % (Ni 64%/$Al_2O_3$) based on substrate concentration. On the contrary, in the process of the present invention the catalyst concentration range can be much lower, as above stated preferably between 0.01 and 0.25 wt % on the same basis, indicating the surprising superior performance of the process of the present invention.

As catalyst is heterogeneous, after completion of the reaction catalyst can be easily removed from the reaction mixture by filtering off, and be repeatedly recycled to the hydrogenation reaction step without need of any further treatment.

The hydrogen partial pressure may be also adjusted in a broad range, which is typically from 1 MPa to 10 MPa, preferably from 2 MPa to 8 MPa, and more preferably from 2 MPa to 5 MPa.

The hydrogenation reaction is suitably performed at temperatures in the range from room temperature to 200° C., preferably from 50° C. to 175° C., more preferably from 50° C. to 125° C.

According to a particular embodiment of the invention the process is carried out with no solvent.

In another particular embodiment the process is carried out in the presence of a solvent selected from water, water-soluble non-acidic solvents and mixtures thereof. In a particular embodiment the water-soluble non-acidic solvent is selected form the group of aliphatic and cycloaliphatic mono- or polyhydric alcohols, more particularly aliphatic and cycloaliphatic mono- or polyhydric alcohols with a number of carbon atoms of up to 5. According to a preferred embodiment, the solvent is 2,3-BDO.

Although solvent concentration can vary in a broad range from 1 wt % to 99 wt % relative to the total amount of solution, preferably the solvent is used in the lowest amount needed for dissolving acetoin at the reaction temperature.

When water is used as solvent, it has to be pointed out that whereas an α-hydroxy ketone concentration lower than 40 wt % is used in the process disclosed in EP 0405956A1, concentrations higher than 40 wt %, even so high as 99 wt %, are used in the process herein disclosed leading to a strong increment in productivity.

The process of the present invention can be advantageously carried out in the presence of no solvent, while keeping the selectivity higher than 90%, even higher than 98%, which is very surprising because in a chemical reaction an increase in substrate concentration favours secondary reactions resulting in a lower selectivity, as it is well known by those skilled in the art. A 100 wt % acetoin concentration can be used directly in the process of the present invention leading to a mixture of heterogeneous catalyst and pure 2,3-butanediol after reaction completion. Consequently, the isolation of pure 2,3-butanediol is simply carried out by filtering off the heterogeneous catalyst.

The hydrogenation reaction may be performed batchwise, semicontinuously or continuously, preferably, semicontinuously or continuously. For batch and semicontinuous operations, reaction time is dependent on hydrogen partial pressure, temperature and catalyst concentration and it can typically vary from 1 h to 45 h. The skilled artisan can determine the reaction time needed for the selected reaction conditions by monitoring the reaction progress.

The skilled person can readily determine for each particular case whether to perform the hydrogenation reaction batchwise, semicontinuously or continuously, and the particular reaction parameters like hydrogen partial pressure, temperature and catalyst concentration without need of any inventive step.

For instance, as reaction rate increases with temperature, hydrogen partial pressure and catalyst concentration, by increasing temperature, or catalyst concentration, or both, a lower hydrogen pressure can be used. Likewise, the same results can be achieved by increasing hydrogen pressure, or temperature, or both, or reaction time, in such a way that a lower catalyst concentration may be used.

According to the present invention an acetoin conversion of at least 40%, preferably of at least 75%, more preferably of at least 90%, much more preferably of at least 95% and even the most preferably of 100% and a 2,3-BDO selectivity (the ratio between yield and conversion) higher than 90%, preferably higher than 95%, and more preferably higher than 98% are obtained.

The process of the invention is a simple, cost effective, clean and sustainable process in which, after reaction completion, 2,3-BDO can easily be isolated in a purity higher than 98%.

The process of the present invention is illustrated below by reference to the examples which are intended to be only illustrative and are not construed to limit the present invention in any way.

EXAMPLES

General Synthetic Procedure

Acetoin, water or 2,3-BDO, if any, and a catalyst in the amounts specified in the examples were charged into a 100 mL jacketed stainless steel autoclave. The autoclave was sealed and 3 times pressurized and depressurized with hydrogen up to a pressure of 0.5 MPa under stirring. Then, the reaction mixture was heated to the desired temperature, the hydrogen pressure adjusted to the target one and the reaction was carried out under stirring during the desired period of time. Temperature was kept constant by recirculating tap water through the reactor jacket as needed by means of an automatic control valve. Two operation modes were studied: a) batchwise, where the hydrogen line between reactor and hydrogen bottle was closed once the desired hydrogen pressure was reached and, therefore, hydrogen pressure inside reactor was continuously decreasing as reaction proceeded; and, b) semicontinuous, where reactor was continuously connected to the hydrogen bottle through its feeding line in such a way that hydrogen pressure inside reactor was always constant throughout the reaction.

All reactions were carried out in Autoclave Engineers Minireactor Assembly Model M010SS60210-E128D-2 consisting in 5 stainless steel minireactors of 100 mL able to work at 20 MPa and 300° C.

After reaction completion, the heating/stirring was stopped and the autoclave cooled to room temperature. The liquid mixture was analyzed by HPLC using a Varian equipment model 920-LC fitted with a refractive index detector, an UV detector and a 30 cm×0.78 cm×9 μm Aminex HPX-87 column. A 0.01N $H_2SO_4$ aqueous solution was used as mobile phase and flow rate was 0.5 mL/min. Column and refractive index detector temperatures were 35° C. and 40° C., respectively. Injection volume was 10 μL. Citric acid was used as internal standard and running time was 40 min. UV detector at 210 nm was used for analyzing acetoin because it was the only chemical detected at such wavelength. 2,3-BDO was analyzed using the refractive index detector. Retention times were as follows: citric acid, 9.43 min; 2,3-BDO: two peaks at 20.66 and 21.98 min, with the first accounting for more than 90% of the total area of both peaks; acetoin, 21.35 min. Calibration lines for acetoin and 2,3-BDO were obtained by using standard solutions of both chemicals in the mobile phase containing 250 mg/L of internal standard. Standard concentration ranges were 300 mg/L-1500 mg/L for acetoin, and 150 mg/L-1500 mg/L for 2,3-BDO.

Metal contents in reaction mixtures after reaction completion were analyzed by ICP.

Examples 1-10

These examples illustrate the very good performance of different catalysts based on Ni and Ru, Pt and Pd supported on alumina, carbon and graphene, according to this invention. Reactions were performed in a semicontinuous mode using 50 g of an aqueous solution of acetoin under the experimental conditions given in table 1, wherein conversions of acetoin (C, %) and yields of 2,3-BDO (Y, %) are also given.

TABLE 1

Performance of different catalysts on acetoin conversion (C, %) and 2,3-BDO yield (Y, %) in acetoin aqueous solutions. $P_{H2}$: hydrogen partial pressure, MPa; T: reaction temperature, ° C.; $C_{cat}$: catalyst concentration, wt % based on the amount of active metal relative to that of acetoin; $C_{ACT}$: acetoin concentration in water, wt %; $t_R$: reaction time (h).

| Example | Catalyst | $P_{H2}$ | T | $C_{cat}$ | $C_{ACT}$ | $t_R$ | C (%) | Y (%) |
|---|---|---|---|---|---|---|---|---|
| 1 | Ru(5%)/$Al_2O_3$[1] | 2 | 175 | 0.5 | 5 | 3.5 | 100 | 94 |
| 2 | Ru(5%)/$Al_2O_3$ | 2 | 175 | 0.5 | 5 | 4.0 | 99 | 99 |
| 3 | Ru(5%)/$Al_2O_3$ | 2 | 175 | 0.5 | 5 | 5.2 | 100 | 93 |
| 4 | Ru(5%)/$Al_2O_3$ | 2 | 175 | 0.5 | 5 | 6.3 | 100 | 96 |
| 5 | Ru(5%)/$Al_2O_3$ | 2 | 125 | 0.125 | 20 | 4 | 100 | 100 |
| 6 | Ru(5%)/Graphene[2] | 2 | 175 | 0.05 | 20 | 16 | 100 | 100 |
| 7 | Ru(5%)/C[3] | 2 | 125 | 0.125 | 20 | 2 | 100 | 94 |
| 8 | Pd(10%)/C[4] | 5 | 175 | 0.5 | 5 | 20 | 40 | 38 |
| 9 | Pt(5%)/$Al_2O_3$[5] | 2 | 175 | 0.5 | 5 | 5.1 | 96 | 93 |
| 10 | Sponge Ni A-7063[6] | 6 | 200 | 0.5 | 20 | 16 | 100 | 100 |

[1] From Degussa type H213 R/D
[2] From NanoInnova Technologies
[3] From Johnson Matthey, Type 600 paste, 54% wet
[4] From Merck
[5] From Alfa Aesar
[6] From Johnson Matthey As it can be seen from Table 1, all catalysts lead to good results with selectivities higher than 93%.

Examples 11-16

These examples further illustrate the performance of ruthenium-based catalysts on alumina and carbon supports. Reactions were performed in a semicontinuous mode using 50 g of a 20 wt % aqueous solution of acetoin at 125° C., a hydrogen pressure of 5 MPa, and variable catalyst concentrations ($C_{cat}$, wt % based on the amount of active metal relative to that of acetoin). Results are given in Table 2, with the symbols having the same meaning than in Table 1.

TABLE 2

Performance of ruthenium-based catalysts. Reaction conditions: 20 wt % aqueous solution of acetoin at 125° C. and 5 MPa.

| Example | Catalyst | $t_R$ (h) | $C_{cat}$ (wt %) | C (%) | Y (%) |
|---|---|---|---|---|---|
| 11 | Ru(5%)/$Al_2O_3$[1] | 3 | 0.250 | 98 | 97 |
| 12 | Ru(5%)/$Al_2O_3$ | 3 | 0.125 | 85 | 85 |
| 13 | Ru(5%)/C[2] | 2 | 0.105 | 100 | 94 |
| 14 | Ru(5%)/C | 2.5 | 0.050 | 100 | 99 |
| 15 | Ru(5%)/C | 2.5 | 0.026 | 100 | 100 |
| 16 | Ru(5%)/C | 2.5 | 0.012 | 100 | 98 |

[1] From Degussa type H213 R/D
[2] From Johnson Matthey, Type 600 paste, 54% wet Results from Table 2 indicate that ruthenium supported on carbon and alumina are both good catalysts according to the invention, with ruthenium supported on carbon having a better performance than that supported on alumina leading to conversions and yields of practically 100% even at a catalyst concentration as low as 0.012 wt %. Likewise, ruthenium concentrations into the reaction mixture were in all cases below 0.1 mg/L as determined by ICP, indicating that catalysts are stable under reactions conditions.

Examples 17-20

These examples illustrate the influence of catalyst concentration. Reactions were performed with ruthenium (5 wt %) on carbon as catalyst in a semicontinuous mode using 50 g of a 20 wt % aqueous solution of acetoin at a hydrogen pressure of 5 MPa and 125° C. for 2.5 h. Results are given in Table 3, with symbols having the same meaning than above.

TABLE 3

Influence of catalyst concentration ($C_{cat}$, wt % based on the amount of active metal relative to that of acetoin). Reaction conditions: 20 wt % aqueous solution of acetoin; 125° C.; reaction time: 2.5 h; catalyst: Ru(5%)/C (paste, 54% wet); $P_{H2}$: 5 MPa.

| Example | $C_{cat}$ | C (%) | Y (%) |
|---|---|---|---|
| 17 | 0.104 | 100 | 94 |
| 18 | 0.050 | 100 | 99 |
| 19 | 0.026 | 100 | 100 |
| 20 | 0.012 | 100 | 98 |

As it can be seen from results in Table 3, Ru(5%)/C keeps its high performance at concentrations as low as 0.012 wt % leading to conversions and yields of 100% and 98%, respectively.

Examples 22-25

These examples illustrate the influence of hydrogen pressure. Reactions were performed with ruthenium (5 wt %) on carbon as catalyst in a semicontinuous mode using 50 g of a 20 wt % aqueous solution of acetoin under the experimental conditions given in Table 4, wherein conversions and yields are also given. As it can be seen, a 100% conversion and a 99% yield are obtained even at a hydrogen pressure as low as 2 MPa and at a mild temperature of 75° C.

TABLE 4

Influence of hydrogen pressure ($P_{H2}$). Reaction conditions: 20 wt % aqueous solution of acetoin; catalyst: Ru(5%)/C (paste, 54% wet). Meaning of symbols as in table 1

| Example | $P_{H2}$ (MPa) | T | $C_{cat}$ | $t_R$ | C (%) | Y (%) |
|---|---|---|---|---|---|---|
| 22 | 4 | 125 | 0.012 | 4 | 100 | 100 |
| 23 | 5 | 125 | 0.012 | 4 | 100 | 100 |
| 24 | 2 | 75 | 0.25 | 8 | 100 | 99 |
| 25 | 3 | 75 | 0.25 | 7 | 100 | 93 |

Examples 26-29

These examples illustrate the influence of temperature. Reactions were performed in a semicontinuous mode under the experimental conditions given in Table 5. Results are also given in Table 5, with symbols having the same meaning than above. As it can be seen, conversions and yields of 100% were obtained even at temperatures as low as 50° C., indicating the very good performance of the process of the invention.

TABLE 5

Influence of temperature. Reaction conditions: 20 wt % aqueous solution of acetoin; reaction time: 4 h; catalyst: Ru(5%)/C (paste, 54% wet); $P_{H2}$: 5 MPa; catalyst concentration: 0.012 wt % (based on the amount of active metal relative to that of acetoin).

| Example | T (° C.) | $P_{H2}$ (MPa) | $C_{cat}$ (wt %) | $t_R$ (h) | C (%) | Y (%) |
|---|---|---|---|---|---|---|
| 26 | 75 | 5 | 0.012 | 4 | 100 | 98 |
| 27 | 100 | 5 | 0.012 | 4 | 100 | 100 |
| 28 | 125 | 5 | 0.012 | 4 | 100 | 100 |
| 29 | 50 | 5 | 0.25 | 8 | 100 | 99 |

Example 30

This example shows that the hydrogenation of acetoin to 2,3-BDO also proceeds with good yields and selectivity at room temperature. Reaction was carried out with ruthenium (5 wt %) on carbon as catalyst in a semicontinuous mode using 50 g of a 20 wt % aqueous solution of acetoin at 25° C. and a catalyst concentration of 0.25 wt % (based on the amount of active metal relative to that of acetoin) and a partial hydrogen pressure of 5 MPa. A 100% acetoin conversion and an 90% 2,3-BDO yield were obtained in 34 h.

Examples 31-34

These examples illustrate the influence of acetoin concentration ($C_{ACT}$, wt %) in water. Reactions were performed in a semicontinuous mode under the experimental conditions given in Table 6. Results are also given in Table 6, with symbols having the same meaning than above. Conversions of 100% and yields higher than 95% were obtained independently of concentration.

Example 34 shows clearly that the reaction can be carried out with pure acetoin, with no solvent, which is a desired embodiment because pure 2,3-BDO is inexpensively and easily obtained by filtering off the catalyst after reaction completion.

TABLE 6

Influence of acetoin concentration ($C_{ACT}$, wt %) using water as a solvent. Reaction conditions: 125° C.; reaction time: 4 h; $P_{H2}$: 5 MPa; catalyst: Ru(5%)/C (paste, 54% wet); catalyst concentration: 0.10 wt % (based on the amount of active metal relative to that of acetoin).

| Example | $C_{ACT}$ (wt %) | $P_{H2}$ (MPa) | C (%) | Y (%) |
|---|---|---|---|---|
| 31 | 20 | 5 | 100 | 100 |
| 32 | 40 | 5 | 100 | 96 |
| 33 | 70 | 5 | 100 | 95 |
| 34 | 100 | 5 | 100 | 98 |

Examples 35-36

These examples show that 2,3-BDO can be used as a reaction solvent for acetoin hydrogenation to 2,3-BDO. Reactions were performed in a semicontinuous mode under the experimental conditions given in Table 7. Results are also given in Table 7, with symbols having the same meaning than above. As it can be seen, conversions of 100% and yields of 98-99% were obtained even at a catalyst concentration as low as 0.01 wt %. Then, isolation of pure 2,3-BDO from reaction mixture after reaction completion can be very easily carried out by filtering off the catalyst.

TABLE 7

Acetoin hydrogenation to 2,3-BDO in 2,3-BDO as a solvent.
Reaction conditions: 75 wt % acetoin concentration in 2,3-BDO;
$P_{H2}$: 2 MPa; catalyst: Ru(5%)/C (paste, 54% wet).

| Example | $C_{cat}$ (wt %) | T (° C.) | $t_R$ (h) | C (%) | Y (%) |
|---|---|---|---|---|---|
| 35 | 0.01 | 125 | 9 | 100 | 98 |
| 36 | 0.01 | 100 | 11 | 100 | 99 |

Example 37

This example illustrates the recyclability of the Ru(5%)/C catalyst. Reactions were carried out in a semicontinuous mode under the experimental conditions given in Table 8. After a reaction was complete the catalyst was removed by filtration and directly recycled to the next reaction. 10 cycles were performed and the results obtained are given in Table 8. As it can be seen the catalyst activity was kept constant throughout the 10 cycles with a mean yield of ~100%. Solutions from all reactions were mixed together and analyzed for ruthenium content yielding a metal concentration less than 0.1 mg/L. As showed in the above examples, yields of ~100% are also obtained with a catalyst concentration of 0.01 wt % which means that catalyst could be recycled at least 1800 reactions according to results obtained in the present example, which shows the huge stability of the ruthenium catalyst under these reaction conditions.

TABLE 8

Recycling of Ru(5%)/C catalyst. Experimental conditions: 50 g of a 20 wt % aqueous solution of acetoin; 125° C.; reaction time: 2.5 h; $P_{H2}$: 5 MPa; catalyst concentration: 0.10 wt % (based on the amount of active metal relative to that of acetoin).

| | Cycle | | | | | | | | | |
|---|---|---|---|---|---|---|---|---|---|---|
| | 1 | 2 | 3 | 4 | 5 | 6 | 7 | 8 | 9 | 10 |
| C (%) | 100 | 100 | 100 | 100 | 100 | 100 | 100 | 100 | 100 | 100 |
| Y (%) | 100 | 100 | 100 | 100 | 100 | 100 | 100 | 97 | 100 | 97 |

Example 38

This example was performed under the same experimental conditions as example 37 but using pure acetoin as raw material instead of a 20 wt % aqueous solution of acetoin. Results are given in Table 9. As it can be seen the catalyst activity was kept constant throughout the 8 cycles with a mean yield of ~99%. Solutions from all reactions were mixed together and analyzed for ruthenium content yielding a metal concentration less than 0.02 mg/L, the detection limit, indicating the huge stability of the ruthenium catalyst under these reaction conditions.

TABLE 9

Recycling of Ru(5%)/C catalyst. Experimental conditions: 30 g of pure acetoin; 125° C.; reaction time: 4 h; $P_{H2}$: 5 MPa; catalyst concentration: 0.10 wt % (based on the amount of active metal relative to that of acetoin).

| | Cycle | | | | | | | |
|---|---|---|---|---|---|---|---|---|
| | 1 | 2 | 3 | 4 | 5 | 6 | 7 | 8 |
| C (%) | 100 | 100 | 100 | 100 | 100 | 100 | 100 | 98 |
| Y (%) | 96 | 100 | 100 | 97 | 100 | 100 | 100 | 96 |

Examples 39-44

These examples illustrate that the reaction can also be carried out batchwise. The reaction was considered complete when hydrogen pressure fall ceased. Experimental conditions and results are given in Table 10, with symbols having the same meaning than above but, in this case, $P_{H2}$ is the initial hydrogen pressure. Catalyst was Ru(5%)/Al$_2$O$_3$.

TABLE 10

Batchwise operation. Experimental conditions: 50 g of an aqueous solution of pure acetoin; reaction time: 4 h; catalyst: Ru(5%)/Al$_2$O$_3$; catalyst concentration: 0.25 wt % (based on the amount of active metal relative to that of acetoin). $C_{ACT}$ (wt %): acetoin concentration

| Example | $C_{ACT}$ (wt %) | T (° C.) | $P_{H2}$ (MPa) | C (%) | Y (%) |
|---|---|---|---|---|---|
| 39 | 5 | 175 | 22 | 97 | 89 |
| 40 | 5 | 175 | 25 | 98 | 88 |
| 41 | 5 | 175 | 35 | 100 | 94 |
| 42 | 5 | 175 | 45 | 100 | 96 |
| 43 | 20 | 125 | 50 | 94 | 90 |
| 44 | 20 | 125 | 60 | 100 | 99 |

The invention claimed is:

1. A process for manufacturing 2,3-butanediol by hydrogenation of acetoin with hydrogen in the presence of a heterogeneous hydrogenation catalyst, in the absence of any carboxylic acid, and (i) in the presence of 2,3-butanediol solvent, or (ii) in the absence of any solvent except for acetoin; wherein the heterogeneous hydrogenation catalyst is Ni or a heterogeneous catalyst supported noble metal.

2. The process according to claim 1, wherein the noble metal is selected from the group consisting of Ru, Pt, Rh, Pd, and their mixtures.

3. The process according to claim 2 where the noble metal is Ru or Pt.

4. The process according to claim 1 wherein the support is selected from the group consisting of carbon, graphite, graphene, graphene oxide, alumina, silica and their mixtures.

5. The process according to claim 1 wherein the support is carbon or alumina.

6. The process according to claim 1 wherein the heterogeneous catalyst is selected from the group consisting of ruthenium supported on carbon, platinum supported on carbon, ruthenium supported on alumina, and platinum supported on alumina.

7. The process according to claim 1 wherein the heterogeneous supported noble metal catalyst is palladium supported on carbon or palladium supported on alumina.

8. The process according to claim 1 wherein the hydrogenation is carried out at a partial hydrogen pressure from 1 to 10 MPa.

9. The process according to claim 1 wherein the hydrogenation is carried out at a partial hydrogen pressure from 2 to 8 MPa.

10. The process according to claim 1, wherein the hydrogenation is carried out at a partial hydrogen pressure from 2 to 5 MPa.

11. The process according to claim 1 wherein the hydrogenation reaction is performed at temperatures in the range from room temperature to 200° C.

12. The process according to claim 1 wherein the hydrogenation reaction is performed at temperatures in the range from 50° C. to 175° C.

13. The process according to claim 1 wherein the hydrogenation reaction is performed temperatures in the range from 50° C. to 125° C.

14. The process according to claim 1, wherein the catalyst concentration is from 0.005 wt % to 0.5 wt %, based on the amount of active metal relative to that of acetoin.

15. The process according to claim 1 wherein the catalyst concentration is from 0.01 wt % to 0.5 wt %, based on the amount of active metal relative to that of acetoin.

16. The process according to claim 1 wherein the catalyst concentration is from 0.01 wt % to 0.25 wt %, based on the amount of active metal relative to that of acetoin.

17. A process according to claim 1 which further comprises a step of filtering off the heterogeneous hydrogenation catalyst.

* * * * *